United States Patent [19]
Barton et al.

[11] Patent Number: 5,923,720
[45] Date of Patent: Jul. 13, 1999

[54] ANGLE DISPERSIVE X-RAY SPECTROMETER

[75] Inventors: Scott W. Barton; Peter M. Calandra, both of Newburyport, Mass.

[73] Assignee: Molecular Metrology, Inc., Newburyport, Mass.

[21] Appl. No.: 08/877,736

[22] Filed: Jun. 17, 1997

[51] Int. Cl.[6] .................................................. G21K 1/06
[52] U.S. Cl. ............................................... 378/84; 378/83
[58] Field of Search ................................. 378/84, 83, 73, 378/45

[56] References Cited

U.S. PATENT DOCUMENTS

| | | | |
|---|---|---|---|
| 4,351,063 | 9/1982 | Dineen et al. | 378/84 X |
| 4,949,367 | 8/1990 | Huizing et al. | 378/84 |
| 5,406,609 | 4/1995 | Arai et al. | 378/84 X |
| 5,619,548 | 4/1997 | Koppel | 378/70 |

OTHER PUBLICATIONS

Lüken et al. "Growth monitoring of W/Si X–ray multilayers by X–ray reflectivity and kinetic ellipsometry" *SPIE* 2253:327 (1994), no month.

Tsuchiya et al. "In–situ X–ray monitoring in MOVPE and feedback grwoth of strained INGaAs".

Picrauz et al. "Structure and Characterization of strained–layer superlattices" *Semiconductors and Semimetal*, 33:139 (1991), no month.

J.H. Underwood and D. Turner "Bent glass optics" *SPIE*, 106:125 (1977), no month.

R.P. Mason and M.W. Trumbore "Differential membrane interactions of calcium channel blockers" *Biochemical Pharmacology* 51:653 (1996), no month.

P.M. DeWolff "Multiple Guinier camera with adjustable curved crystal monochromator" in *Selected Topics on X–Ray Crystallography*, Ch. 3, ed. J. Bouman (North–Holland, Amsterdam, 1951), no month.

Shenfil et al. "A point focusing X–ray monochromator for the study of low angle diffraction" *J. Appl. Physics* 23(8):854 (1952), no month.

*Primary Examiner*—David P. Porta
*Attorney, Agent, or Firm*—Choate, Hall & Stewart

[57] ABSTRACT

An x-ray spectrometer is provided comprising an X-ray source, a curved crystal monochromator which focuses a monochromatic x-ray beam onto a sample surface, the curved crystal monochromator comprising a shape which is substantially identical to a logarithmic spiral, and a position-sensitive x-ray detector. A method of measuring diffraction intensities from oriented samples in real time including providing an x-ray spectrometer comprising an X-ray source, a curved crystal monochromator which focuses a monochromatic x-ray beam onto a sample surface, the curved monochromator comprising the shape of a logarithmic spiral, and a position-sensitive x-ray detector; and providing a crystallographically oriented sample, exposing the sample to the focused x-ray beam of the x-ray spectrometer; and measuring the diffraction intensity at the position-sensitive detector.

36 Claims, 4 Drawing Sheets

$$W_1 = W_0 + \frac{(Acryst)(L)}{2}$$

$$W_2 = W_0 - \frac{(Acryst)(L)}{2}$$

$$\emptyset_1 = \frac{dx}{R_1}$$

$$\emptyset_2 = \frac{dx}{R_2}$$

$$\emptyset_3 + \emptyset_2 + \emptyset_4 = 180$$

$$\emptyset_3 + \emptyset_1 + (\emptyset_4 + \emptyset) = 180$$

$$\emptyset_2 - \emptyset_1 = \emptyset$$

$$d\emptyset = dx \left\{ \frac{1}{R_2} - \frac{1}{R_1} \right\}$$

ANGLE DISPERSIVE X-RAY SPECTROMETER

BACKGROUND OF THE INVENTION

1. Field of Invention

The present invention is directed toward the field of x-ray diffraction as a versatile tool to determine the structure of atomic and superlattice systems with preferred orientation along at least one dimension. The invention may be configured for the determination of structure in lipid membranes, in-situ thickness measurements of thin films during growth, and determination of lattice mismatch in epitaxial crystalline films.

2. Description of the Prior Art

X-Ray diffraction has been used to measure in situ thickness of thin films during deposition (Lüken, et. al., SPIE Vol. 2253:327 (1994)). Lüken et al. describe an angle dispersive x-ray reflectometer which employs a Johansson-type (T. Johansson, Zeit. Physik, 82:507 (1933)) curved crystal monochromator to focus and wavelength-select X-radiation, with a convergence angle of 2.5° ($4.4 \times 10^{-1}$ radians), down to a silicon substrate surface on which a W/Si multilayer is grown. The Johansson-type crystal is one in which the reflecting surface is ground to a radius of curvature 2R and the crystal is subsequently bent to a radius of curvature R. The low angle x-ray reflectivity is monitored from the Si substrate simultaneously between 0° and 2.5° using a linear position sensitive charge-coupled device (CCD) detector. The authors used the instrument to monitor the growth of the multilayer in-situ during evaporative deposition.

While in principle, the Johansson crystal provides "perfect" point-to-point focusing, there are limitations to using Johansson crystals. For example, the size of the beam at the focus is approximately the same size as the source. For a fine focus x-ray source, with a target source size of $0.4 \times 8$ mm$^2$, this dimension at a 6° (0.10 radians) takeoff angle is defined by (0.4 mm)Sin(0.10) and has a value of about 42 $\mu$m in the focusing plane. To further reduce the focus, the effective source size would need to be reduced with a slit to block part of the radiation. Not only would the use of a slit diminish the intensity of the x-ray beam, but alignment is now made considerably more difficult, since the monochromator and the sample need to be positioned to within microns with respect to the source in order to take advantage of the small focus. Furthermore, because the crystal monochromator surface must be ground and bent to a very specific curvature, there is, for practical purposes, no forgiveness built into the design to compensate for misalignments or bending error. Thus, the requirement that the surface be ground and then bent makes the fabrication expensive.

Small angle x-ray scattering has been used to measure structure in oriented lipid bilayers (Mason and Trumbore, Biochemical Pharmacology 51:653 (1996)). Using small-angle x-ray spectrometry, Mason and Trumbore report the sensitivity of the method to indicate the incorporation and location of antioxidants into the lipid matrix. To achieve the orientation, multilayer stacks of the lipid bilayers are centrifuged down onto a flat substrate from vesicles suspended in an aqueous medium. The lipids are found to align spontaneously with the stacking axis normal to the substrate surface. The substrate is made from a bendable sheet of aluminum which is subsequently mounted on a curved glass surface (radius of curvature c.a. 20 mm). An incident x-ray beam is then focused with a bent grazing incidence mirror to illuminate the curved substrate with an intense beam of small, but unspecified, angular divergence. Different parts of the incident beam intersect the curved surface at different angles of incidence, and the scattering from the entire beam is measured on a position-sensitive x-ray detector which measures the intensity as a function of linear position along the detector axis. The discrete diffraction peak intensities are then Fourier transformed to determine the electron density profile within the lipid bilayer. Mason and Trumbore report the difference in electron density between the oriented lipid lamellar stack incubated in the vesicle state without antioxidant and the same lipid incubated with the target antioxidant in the vesicular suspension before centrifugation.

While this method is able to capture all the relevant diffraction information, the technique suffers from the time-consuming step of gluing the aluminum substrate to the curved glass surface. Furthermore, the x-ray beam is not monochromatic, but is simply filtered to significantly reduce the $K_\beta$ radiation. The dominant radiation which diffracts from the sample is the $K_{\alpha 1}/K_{\alpha 2}$ doublet. The continuous brehmstrahlung background radiation, particularly at energies between 4 and 8 keV, remains. This continuous spectrum radiation increases the background signal on top of which the diffraction peaks are observed and this subsequently diminishes the ability to observe weak diffraction lines and accurately determine integral peak areas.

High resolution, wide angle x-ray scattering is commonly used to determine the lattice parameters in epitaxially grown films (in particular, strained-layer superlattices) with respect to the lattice of the single crystal substrate. The typical approach is to employ a two-crystal spectrometer (monochromator and sample) and measure a rocking curve of the sample in the vicinity of a Bragg diffraction angle from the sample substrate. These angles are typically in the range of 30° to 50° and the rocking curve scan is performed over a range of several degrees. During the rocking scan, the diffraction intensities are measured using a scintillation detector with an entrance slit large enough to accept diffraction over an angular range of several degrees. The wide detector slit precludes the ability to know the diffraction angle precisely. As a result, satellite peaks and orientation of reciprocal lattice vector in strained-layer superlattices are not readily discernible.

Picreaux et al. (Semiconductors and Semimetals, 33:139 (1991)) employ a linear position-sensitive x-ray detector (PSD) to measure diffraction intensities from epitaxial films in rocking curve scans with a high resolution two-crystal x-ray spectrometer. While the use of the PSD provides information to allow reciprocal space mapping of the epitaxial layers, the method still requires illumination of the substrate with a highly collimated, monochromatic beam and then measuring the diffraction intensities while step scanning the sample tilt one angle at a time; this approach is both complicated and time-consuming.

Using a high resolution, two-crystal x-ray spectrometer, Tsuchiya et al. (Proc. 4th Indium Phosphide and Related Materials Conf., Newport, R.I., 1992) describe feedback control used to adjust the growth conditions during deposition of a vapor phase epitaxial grown film of InGaAs on a single crystal substrate, InP. A scintillation detector with a wide slit was used and the entire x-ray source and monochromator optics were rotated about the sample in order to perform the rocking curve scans. While this method demonstrates the feasibility of using x-ray diffraction for deposition feedback, rotation of the x-ray source about the sample is cumbersome and limits the amount of space available for the deposition system. Furthermore, the method is impractical for faster deposition, since the incident angles are stepped one at a time.

X-rays may be simultaneously focused and monochromatized by reflecting a divergent x-ray beam from a curved single crystal such that incident beam intersects the crystal at the Bragg diffraction angle for the desired wavelength. An ideal shape for such a focusing x-ray monochromator is for the crystal curvature to be identical with a logarithmic spiral. DeWolff (*Selected Topics on X-Ray Crystallography*, Ch. 3, ed. J. Bouman, North-Holland, Amsterdam, 1951) describes a four-point crystal bender to approximate the ideal logarithmic spiral form for a focusing monochromator crystal to second order with respect to the local crystal curvature. This monochromator design has been employed for almost half a decade in powder diffraction spectrometers. The bending design is simple, robust, and in contrast to the Johansson-type focusing, the logarithmic spiral does not require a true point x-ray source.

The main disadvantage of this type of focusing monochromator is that the focusing quality can not be improved beyond that already accomplished with the conventional four-point bending apparatus. This inherent limitation is due to the difference in functional form between the ideal logarithmic spiral and the shape that the monochromator can assume in a mechanical, four-point bending apparatus.

X-rays are totally reflected from smooth mirror surfaces when the x-rays illuminate the mirror below a grazing incident critical angle. For hard x-rays (>1 keV), this angle is typically on the order of a few tenths of a degree. Underwood and Turner (SPIE, 106:125 (1977)) describe how bent, nondiffracting mirror surfaces can made to focus or collimate x-rays more efficiently by grinding the sides of the mirror such that the width of the reflecting surface varies as function of the length. This shaping procedure is used to "tune" the moment of inertia as a function of length, and allows a bending system to more accurately define the shape of the mirror to the ideal parabola or ellipse. The authors intended this design to be used in astrophysical applications for x-ray telescopes; and these mirror focusing elements differ significantly from diffracting crystal optics.

Thus, there remains a need for an x-ray spectrometer with a curved crystal monochromator which can provide improved point focusing of the x-ray source and micron scale scanning of the sample surface. There is a further need for methods of preparing curved crystals having a curvature of a logarithmic spiral which overcome the inherent limitations of the prior art.

SUMMARY OF THE INVENTION

It is the object of the present invention to provide an x-ray spectrometer which provides superior point focusing of a source x-ray beam from a real extended source.

It is a further object of the invention to provide a curved single crystal or other dynamically diffracting element for use as an x-ray monochromator having a surface curvature which most nearly approximates a logarithmic spiral. Dynamical diffraction includes diffraction from perfect crystals, like silicon germanium and lithium fluoride, as well a reflection from synthetic multilayers, such as W/Si alternating film stacks.

It is yet a further object of the invention to provide an x-ray reflectometer which permits data accumulation over a range of angles incident to the sample surface in a single measurement.

It is yet a further object of the invention to provide a method of measuring x-ray reflectance or x-ray diffraction over a range of incident angles to the sample surface in a single measurement.

It is yet a further object of the present invention to provide an improved and more efficient method of determining electron density profiles in lipid layers.

It is yet a further object of the present invention to provide an improved and more efficient method of determining epitaxial film structure and growth.

These and other objects of the invention are accomplished by use of the x-ray spectrometer described herein. Unique features of the invention are intended to make it possible to reduce the data collection times several orders of magnitude and perform diffraction scanning with resolution on the order of microns in the scanning direction.

By "logarithmic spiral", it is meant a mathematically defined surface curvature that is often occurring in nature. Diverse objects such as snail shells, fiddlehead ferns and other naturally occurring elements follow the shape of the logarithmic spiral; while the curvatures described in this disclosure are of the logarithmic spiral form, the radius of curvature is orders of magnitude larger than those found in nature.

An advantage of the present invention is that the x-ray source need not be a point in order to obtain high resolution. This is an advantage as most real laboratory x-ray sources are extended and not point sources. In addition, due to the ability to simultaneously collect date over a range of incident angles, data collection is much more rapid than in conventional spectrometers.

In one aspect of the invention, an x-ray spectrometer is provided which includes an x-ray source; a curved crystal monochromator which focuses a monochromatic x-ray beam onto a sample surface, the curved crystal monochromator comprising a shape which is substantially identical to a logarithmic spiral; and a position-sensitive x-ray detector positioned to receive x-ray beams diffracted or reflected from a sample surface. Whether or not the source x-ray beam is diffracted or reflected is a function of the angle of incidence of the x-ray beam on the sample.

In preferred embodiments, the width of the curved crystal monochromator is linearly tapered along an arclength s of the crystal. In other preferred embodiments, width of the the curved crystal monochromator has a taper selected to minimize a third order difference in s between an ideal logarithmic spiral curve and the curved crystal. The monochromator crystal may be shaped along its length in a form other than rectangular. The taper of the crystal monochromator may be a taper less than about 100 milliradians and preferably about 20 milliradians.

In other preferred embodiments, a linear position-sensitive proportional detector is used. The position-sensitive detector may be a linear photodiode array, a linear charge coupled device, a two-dimensional proportional x-ray detector, or a two-dimensional charge coupled device. The spectrometer may also include at least one single slit is positioned between the x-ray source and the monochromator and a plurality of slits may be positioned in front of the monochromator.

In other preferred embodiments of the invention, the x-ray spectrometer includes a sample which may be an epitaxially grown layer, an evaporated layer, an epitaxially grown multilayer or superlattice, or a multilayer deposited by evaporation. The x-ray spectrometer may be attached as an accessory to a larger film deposition system and the film parameters determined by the spectrometer may be used to control the deposition of a film.

In other preferred embodiments, the x-ray spectrometer may be adapted oriented to measure x-ray reflectivity from horizontal surfaces (i.e., liquids) or for scanning in the lateral direction. The x-ray spectrometer may additionally include a second focusing device, such as a curved mirror, positioned so as to focus in the plane substantially perpendicular to the curved crystal monochromator. The second focusing device may be a curved crystal monochromator.

In another aspect of the invention, a curved crystal monochromator is provided which focuses a monochromatic x-ray beam onto a sample surface, wherein the curved crystal monochromator comprises a shape substantially identical to a logarithmic spiral as measured along the crystal monochromator length, wherein the width of the curved crystal monochromator is linearly tapered along an arclength s of the crystal. In preferred embodiments, the curved crystal monochromator has a taper selected to minimize a third order difference in s between an ideal logarithmic spiral curve and the curved crystal. The monochromator crystal may be shaped along its length in a form other than rectangular. The monochromator crystal may have a taper less than about 0.10 radians, and preferably less than 0.02 radians.

In another aspect of the invention, a method for measuring electron density in a lipid layer is provided by providing an x-ray spectrometer comprising an X-ray source; a curved crystal monochromator which focuses a monochromatic x-ray beam onto a sample surface, the curved monochromator comprising the shape of a logarithmic spiral; and a position-sensitive x-ray detector; and providing a sample comprising single or multilamellar lipid layers deposited on a flat substrate; exposing the sample to the focused x-ray beam of the x-ray spectrometer and measuring the diffraction intensity at the position sensitive detector.

In preferred embodiments, the sample may be natural or synthetic lipids, natural or synthetic lipids deposited by centrifugation from solution or suspension, a lipid deposited by Langmuir-Blodgett deposition, or a lipid deposited by self-assembly from solution.

In yet another aspect of the invention, a method of measuring diffraction intensities from oriented samples in real time is provided by providing an x-ray spectrometer comprising an X-ray source; a curved crystal monochromator which focuses a monochromatic x-ray beam onto a sample surface, the curved monochromator comprising the shape of a logarithmic spiral; and a position-sensitive x-ray detector; and providing a crystallographically oriented sample; exposing the sample to the focused x-ray beam of the x-ray spectrometer; and measuring the diffraction intensity at the position-sensitive detector.

BRIEF DESCRIPTION OF THE DRAWING

The invention is described with reference to the following Figures, which are provided for the purposes of illustration only and which are not intended to be limiting of the invention, and in which.

DETAILED DESCRIPTION OF THE INVENTION

Figure 1:
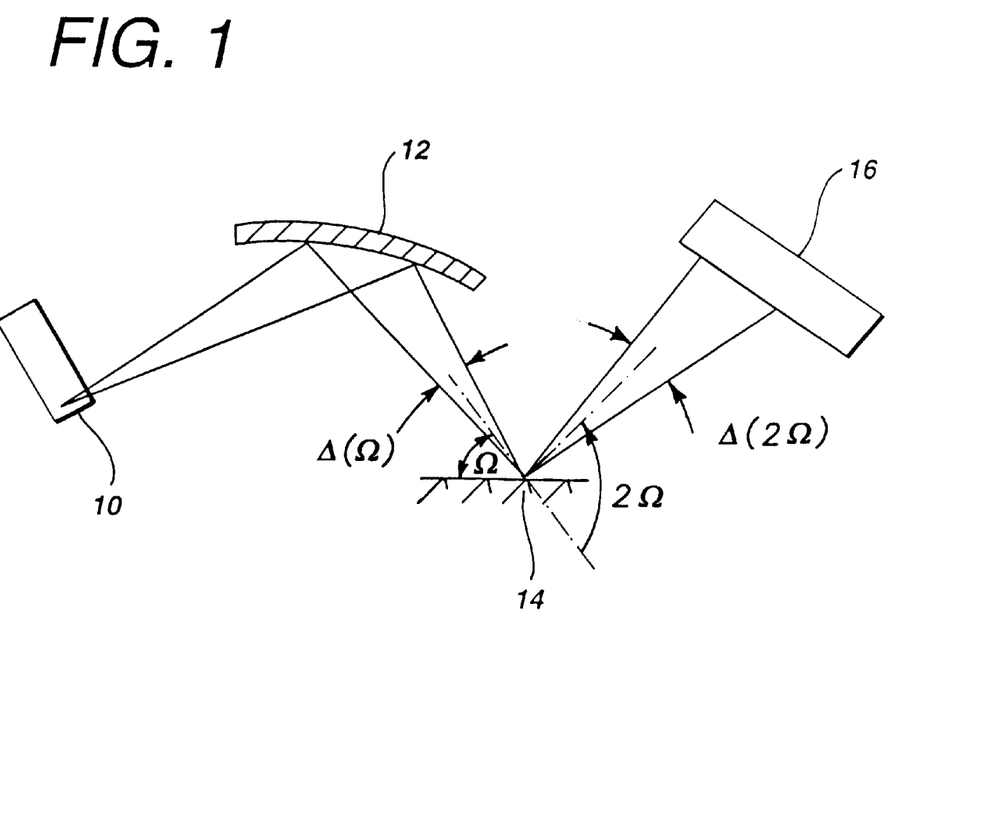
FIG. 1 is a schematic illustration of the x-ray spectrometer of the invention.

The present invention is designed to perform angle dispersive x-ray diffraction and is composed of several components shown in FIG. 1. X-rays emanating from an x-ray source 10 are focused by a curved crystal monochromator 12, with the unique design that will be described presently below. The x-rays are focused onto a sample specimen 14 which has a well-defined periodicity along the z-axis. Diffracted intensities from the sample within an angular range defined by the focus convergence are detected simultaneously at different diffraction angles on a position-sensitive x-ray detector 16.

The x-ray sources hereinafter referred to as the "source" may be sources well-known in the art such as sealed x-ray tubes or rotating anodes. In x-ray laboratory sources, a common source is $CuK_\alpha$ radiation, but the source could equally be generated from molybdenum, silver, chromium, rhodium, iron and other target materials. The convergence of the monochromator focus and the focal size are dependent upon x-ray energy and also the orientation of the reflecting atomic planes to the monochromator surface. These features are taken into consideration in the analysis which follows.

Position sensitive detectors which are known in the art are suitable for use in the x-ray spectrometer of the invention. Suitable position sensitive detectors include linear position-sensitive proportional detectors, linear photodiode arrays, linear charge coupled devices, two-dimensional proportional x-ray detectors, two-dimensional charge coupled devices.

The x-ray spectrometer of the invention is useful in analyzing any material which exhibits a well-defined periodicity along at least one dimension. By way of example only, the sample includes natural or synthetic lipids, epitaxially grown layers, evaporated layers, and epitaxially grown multilayers or superlattices. The sample surface may be a solid or a liquid; in the latter case, the sample is horizontal within the spectrometer.

The monochromator crystal desirably is a perfect single crystal, the exact composition of which may be chosen according to the needs of the particular application. Single crystal germanium, silicon and lithium fluoride are preferred single crystals for use in the present invention. The crystal is oriented along a selected diffraction plane; however, the particular diffraction plane is not of great significance to the invention. Orientation of the crystal monochromator will have an effect on the diffracting angle of the crystal, which may be taken into consideration in the curvature of the crystal as discussed below. In addition, it is recognized that certain synthetic multilayers may be used in place of the perfect crystal. These multilayers may consist of alternating thin films of two or more materials, e.g., Si/W deposited on a thin bendable substrate.

Figure 2:
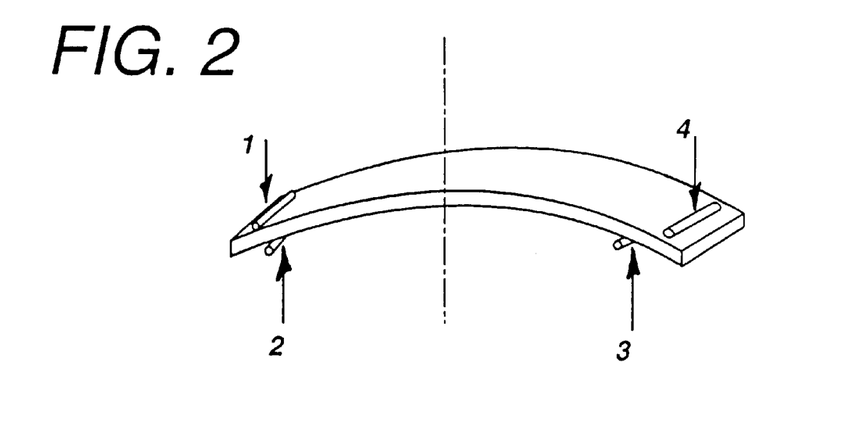
FIG. 2 is a schematic illustration of the four-point bending technique used to shape a curved crystal monochromator.
Figure 3:
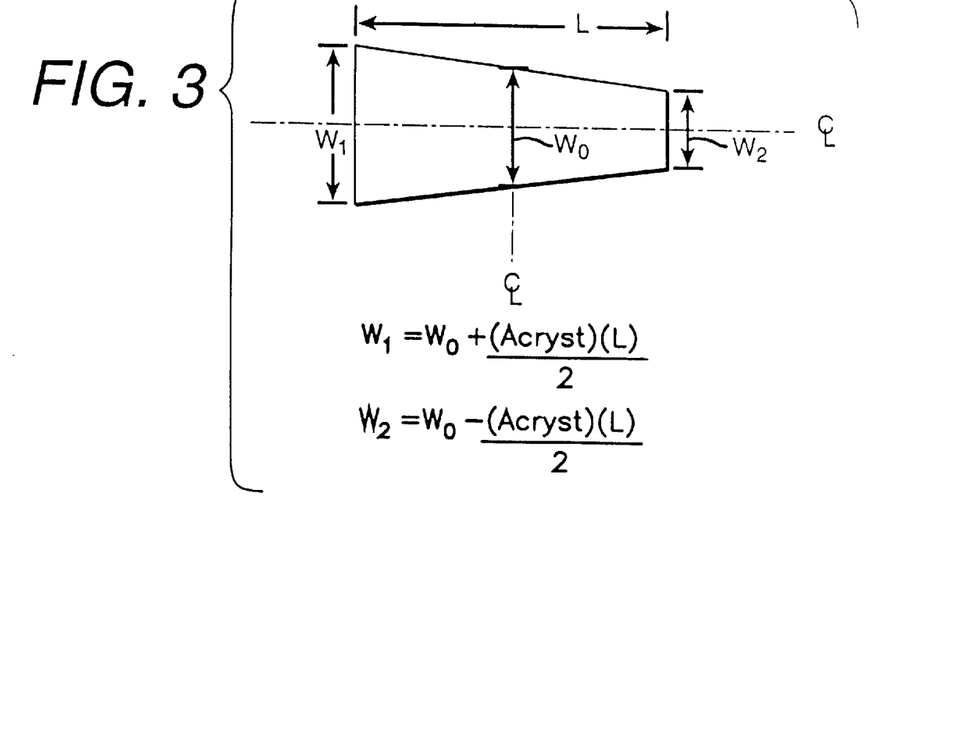
FIG. 3 is a plan view of a linearly tapered crystal of the invention prior to bending.

The monochromator with dimensions as shown in FIG. 3 is bent by a four point bender (shown schematically in FIG. 2) to assume the shape which substantially approximates that of a logarithmic spiral which provides perfect focusing from an extended source. This is in contrast to the Johansson-type monochromator (described by Luken et al.) which requires a point source to achieve perfect focusing. Since real laboratory x-ray sources have a finite size, the logarithmic spiral form is better suited for laboratory experiments.

Prior to subjecting the monochromator crystal to a four-point bending process in order to approximate a logarithmic spiral curvature, the sides of the monochromator crystal which define the width are ground in order to bend the real monochromator to a shape which significantly improves the mechanical approximation to the ideal logarithmic spiral. The shaping introduces a taper and preferably a linear taper along the length of the crystal. The taper is selected commensurate with the application of the apparatus, the composition of the crystal, the wavelength of the x-ray and the geometry of the spectrometer; however, tapers of less than 0.10 radians and preferably less than 0.02 radians are typical. A crystal exhibiting an exemplary taper of the invention is shown in FIG. 3. Referring to FIG. 3, in which the unbent, flat crystal is shown in plain view, L is defined as the length of the monochromator crystal, $W_0$ is the width of the crystal at the center line (CL) of the crystal, $W_1$ is the width of the crystal at its larger end and $W_2$ is the width of the crystal at its smaller end. For the unbent crystal shown in FIG. 3, the width dimension of the coincident along the y-axis, the length L is coincident along the x-axis and the thickness is coincident with z-axis. A linear taper is defined by and angle $\tau = \arctan\{(W_1-W_2)/L\}$. These dimensions are indicated in FIG. 3. This new design produces a beam focus which is at least an order of magnitude smaller than that described in the prior art (de Wolff), without a restriction in the source size; furthermore, the focus quality of the present invention makes it possible to perform x-ray diffraction and x-ray reflection in a high resolution scanning mode.

The taper may be introduced into the crystal using standard crystal handling techniques. For example, the crystal may be securely mounted in a clamping device in a surface grinding apparatus. The edge of the crystal is indicated with a dial indicator which is a sensitive spring-loaded mechanical measuring tool. Such instruments can determine the relative displacement of a surface to 0.0005" (0.5 mil) or less. The crystal may then be tilted until the edge has the desired relative displacement from one end to the other corresponding to the desired taper. The taper is introduced by applying a grinding surface such as a diamond grinding wheel across the crystal edge. The process is then repeated on the other side of the crystal. A camera-equipped apparatus, such as an optical comparitor, may be used for such an operation.

Figure 4:
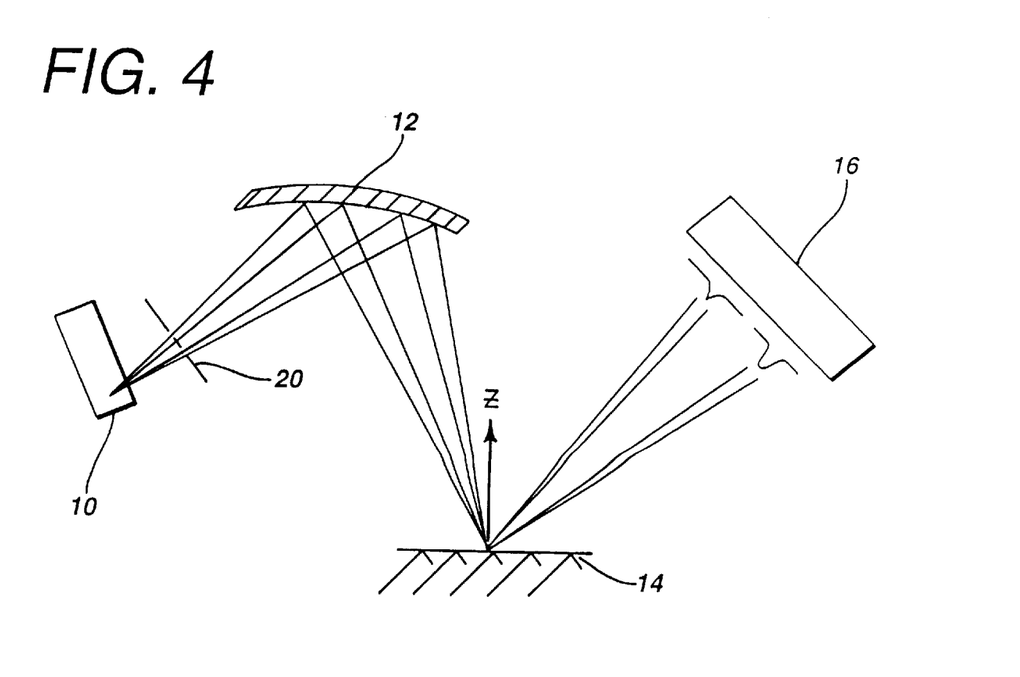
FIG. 4 is a schematic illustration of another embodiment of the x-ray spectrometer of the invention.

For sample specimens in which diffuse scattering distorts or prohibitively increases the background intensity relative to the specular intensity, a single or "ladder" slit 20 can be used to determine the integrated specular scattering above the background, as is shown in FIG. 4. The slit 20 serves to define a beam with an angular convergence much smaller than that defined over the entire monochromator. The purpose is to create a highly collimated beam which is incident on the sample at a specific angle. One would observe on the PSD a single well-defined peak corresponding to the specularly reflected beam. One or more slits may be employed in the spectrometer, as needed. The method and apparatus may be adapted for use with a solid or a liquid sample.

In addition, the spectrometer may include a second focusing device. The second focusing device typically is positioned within the spectrometer so as to focus in the plane substantially perpendicular to the curved crystal monochromator. This provides focus along a second axis resulting in a reduced spot size of the x-ray beam. The reduced spot size makes the spectrometer well suited for used as a diffraction microprobe. The second focusing device may be any conventional focusing crystal or mirror. In a preferred embodiment, it may also be a curved crystal monochromator of the type described herein.

Figures 5, 6:
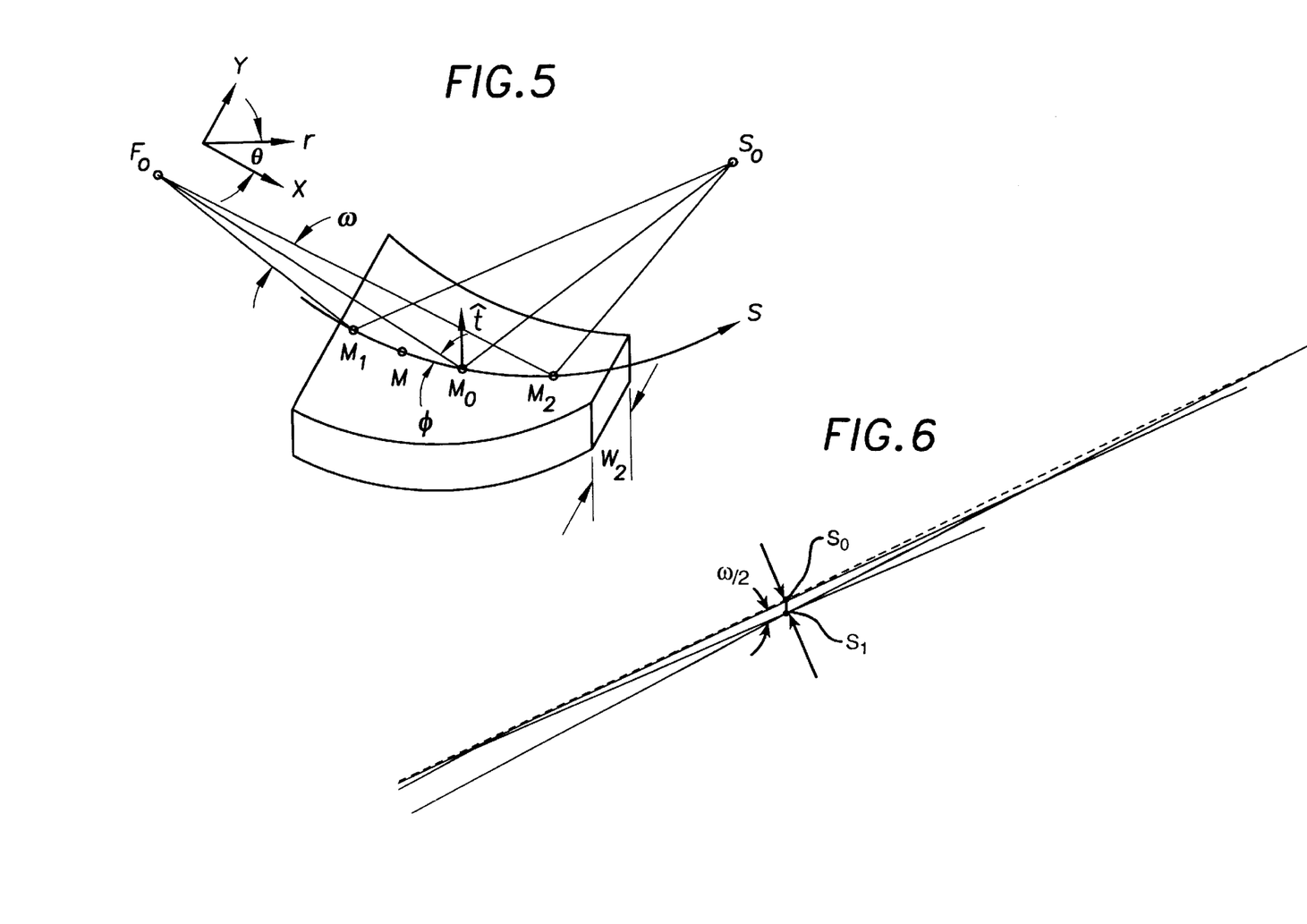
FIG. 5 is an illustration of the diffractive relationships in the x-ray spectrometer of the invention.
FIG. 6 is an enlarged illustration of the diffractive relationships in a portion of the x-ray spectrometer of the invention.

The log spiral (LS). The specific curvature for the LS monochromator is determined by 1) the desired x-ray wavelength, and 2) the orientation of the crystallographic diffraction planes with respect to the monochromator surface and 3) the monochromator/source and monochromator/focus distances. The important feature of the logarithmic spiral is that the angle, $\phi$, formed between a vector from the origin and the tangent to any point on the spiral curve is constant. In FIG. 5, this geometry is realized for the present spectrophotometer by providing a crystal monochromator having an ideal logarithmic spiral with the origin representing a focus on a sample surface, $F_0$. For the general case where the diffracting crystallographic planes of the monochromator are oriented at an angle $\sigma$ with respect to the monochromator surface, the constant grazing angle of incidence is given as:

$$\phi = \theta_{BRAGG} - \sigma, \tag{1}$$

where $\theta_{BRAGG}$ is the Bragg angle of diffraction for the monochromator and $\sigma$ is the orientation angle of diffracting crystallographic planes with respect to the monochromator surface, and where the Bragg angle of the monochromator for a given wavelength and diffraction plane is:

$$\theta_{BRAGG} = \sin^{-1}\left(\frac{\lambda}{2d}\right), \tag{2}$$

where $\lambda$ is the x-ray wavelength and d is the characteristic atomic spacing between the monochromator's diffraction plane.

For the purposes of this disclosure, a quantitative description of the LS is presented in order to demonstrate the ability of this invention to achieve micron scale focal dimensions. The mathematical representation of the LS has the following form in polar coordinates $(r,\theta)$ where r is the polar distance from origin to a point on the logarithmic spiral; $\theta$ is the polar angle of the logarithmic spiral; and $\alpha$, $\beta$ are constants:

$$r = \alpha e^{\beta\theta}, \tag{3}$$

which can be written parametrically in Cartesian coordinates, (x,y), as a function of $\theta$:

$$\left.\begin{array}{l}x = \alpha e^{\beta\theta}\cos(\theta)\\y = \alpha e^{\beta\theta}\sin(\theta)\end{array}\right\}, \tag{4}$$

assuming the geometry shown in FIG. 5, with the focus placed at the origin and the center of the crystal positioned at $x=\alpha=\overline{F_0M_0}$ and $y=0$. $\overline{F_0M_0}$ represents the distance from the center of the monochromator crystal ($M_0$) to the sample surface ($F_0$). $F_0$ also coincides with the origin corresponding to the ideal logarithmic spiral.

The constant $\beta$ is a function of the constant $\phi$ and determined from the scalar product between the unit ray along $\overline{F_0M}$:

$$\hat{u} = \cos\theta\hat{i} + \sin\theta\hat{j}, \tag{5}$$

and the unit tangent at M where M represents an arbitrary point on surface of the monochromator:

$$\hat{f} = \left[\frac{\beta\cos(\theta) - \sin(\theta)}{\sqrt{\beta^2 + 1}}\right]\hat{i} + \left[\frac{\beta\sin(\theta) + \cos(\theta)}{\sqrt{\beta^2 + 1}}\right]\hat{j}, \quad (6)$$

where $\hat{i}$ and $\hat{j}$ are unit vectors in the x and y directions, respectively. Thus, $$\cos(\varphi) = \hat{t} \cdot \hat{u} = \frac{\beta}{\sqrt{\beta^2 + 1}} \quad (7)$$

$$\Rightarrow \beta = \pm\cot(\varphi). \quad (8)$$

By the present convention in which a clockwise rotation of $\theta$ is negative, the positive value for $\beta$ is chosen.

Of additional relevance to this disclosure are the arclength, s, along the logarithmic spiral axis:

$$s(\theta) = \frac{\alpha\sqrt{\beta^2+1}}{\beta}[e^{\beta\theta} - 1] \quad (9)$$

and the radius of curvature, $R_{LS}(\theta)$:

$$R_{LS}(\theta) = \alpha e^{\beta\theta}\sqrt{\beta^2+1} = s\beta + \alpha\sqrt{\beta^2+1}, \quad (10)$$

where $R_{LS}(\theta)$ is the radius of curvature at the point on the spiral defined by $\theta$.

For our exemplary case of the diffractometer design, we choose a copper x-ray source with a germanium single crystal monochromator selecting the Cu $K_{\alpha1}$ radiation (1.5407 Å), reflecting from the Ge(111) crystallographic planes. A symmetric reflection geometry for the LS will be adopted, where $\phi = \theta_{BRAGG} = 13.63°$ (0.2379 radians). The distances $\overline{F_0M_0} = \overline{M_0S_0}$ as represented in FIG. 5 may be typically 165 mm. One of the advantages of the LS monochromator is that it views an extended x-ray source, shown in FIG. 6 as the line at $S_0S_1$. The x-ray source size in a conventional laboratory system is defined by the rectangular portion of a target on which is focused an accelerated electron beam. In a typical configuration of this invention, a Cu x-ray tube with target dimensions 2 mm×12 mm may be employed. The tube may be tilted so that the monochromator views the 2 mm dimension from a takeoff angle of 10° (0.174 radians), making the effective source size seen by the monochromator equal to (2 mm)Sin(0.174)=0.35 mm. Based on this value, a typical 30 mm length of the crystal will collect and reflect a fan of radiation with a convergence angle, ω, equal to 0.045 radians (de Wolff). The radius of curvature of the monochromator at $M_0$ is 700 mm. A 0.5 mm thick crystal may be used.

The x-ray focus characteristics are determined by the quality of the match between the bent crystal and the ideal logarithmic spiral. By using a four-point bending apparatus, de Wolff approximated the ideal logarithmic shape to second order in s (de Wolff). In this invention disclosure, we describe a method by which the logarithmic shape can be bent to a vanishingly small third order term for the best case; and even if the best case situation can not be met exactly, a finite but small second order term remains, but this term is at least one order of magnitude less than the remainder term in the prior art. It is precisely this focusing geometry that makes micron resolution scanning possible with our invention.

Below we demonstrate that the focus in our new monochromator design is superior to that described in the prior art. We first describe the radius of curvature for the longarithmic spiral monochromator crystal (equation 10) in the form:

$$R_{LS} = R_{0,LS}(1 + A_{LS}s) \quad (11)$$

where $$R_{0,LS} \equiv \alpha\sqrt{\beta^2 + 1} = \frac{\overline{F_0M_0}}{\sin\varphi} \quad (12)$$

$$A_{LS} \equiv \frac{\beta}{\alpha\sqrt{\beta^2+1}} = \frac{\cos\varphi}{\overline{F_0M_0}}$$

and $R_{0,LS}$ is the radius of curvature at s =0, at the center of the crystal and $A_{LS}$ is the coefficient of s in equation (11) for the radius of curvature for the logarithmic spiral.

This curvature radius is compared to that for a four-point bender in which two adjustable loads are applied evenly across the crystal width and symmetric about the center line of the crystal, with two symmetric supports across the width, but closer to the center than where the adjustable loads are applied (see FIG. 2). The prior art (de Wolff, Lüken et al.) employ a rectangular shaped crystal monochromator. Our invention employs a linearly tapered crystal such that the moment of inertia I along the bending axis, x, is:

$$I = \frac{wt^3}{12}(1 + A_{cryst}x) \equiv I_0(1 + A_{cryst}x), \quad (13)$$

where w is the width of the crystal, t is the thickness and $A_{cryst}$ is the slope of the taper. It is apparent that, for the prior art crystal where the taper $A_{cryst}=0$, the moment of inertia is the same along the length of the crystal, whereas for the crystal monochromator of the invention, the moment of inertia varies along the axis of bending.

From elementary beam theory, the curvature of the linear taper crystal at point x, along the bending axis bent in the described four-point bender is:

$$R_{cryst} = \frac{EI_0(1 + A_{cryst}x)}{L_0(1 + B_{cryst}x)}, \quad (14)$$

where $L_0$ is the bending moment (the change in bending moment of inertia along the taper) at the crystal center, E is the Young's modulus of the monochromator, $I_0$ is the bending moment of inertia at the crystal center, and $B_{cryst}$ is the slope of the bending moment from point 2 to point 3 in FIG. 2 introduced by unequal loading at points 1 and 4 in FIG. 2. We recognize that the curvature for the ideal LS form (equation 11) is cast as a function of s, while the dimension, x, described in equation 14 is measured along the axis perpendicular to the reaction forces. The two lengths differ in third order:

$$x = s - \frac{s^3}{6R^3} + O\left(\left[\frac{s}{R}\right]^4\right). \quad (15)$$

The best match between the logarithmic spiral and the real crystal will be given when $$\frac{EI_0}{L_0} = R_{0,cryst} = R_{0,LS}, A_{cryst} = A_{LS}, \text{ and } B_{cryst} = 0.$$

Figure 7:
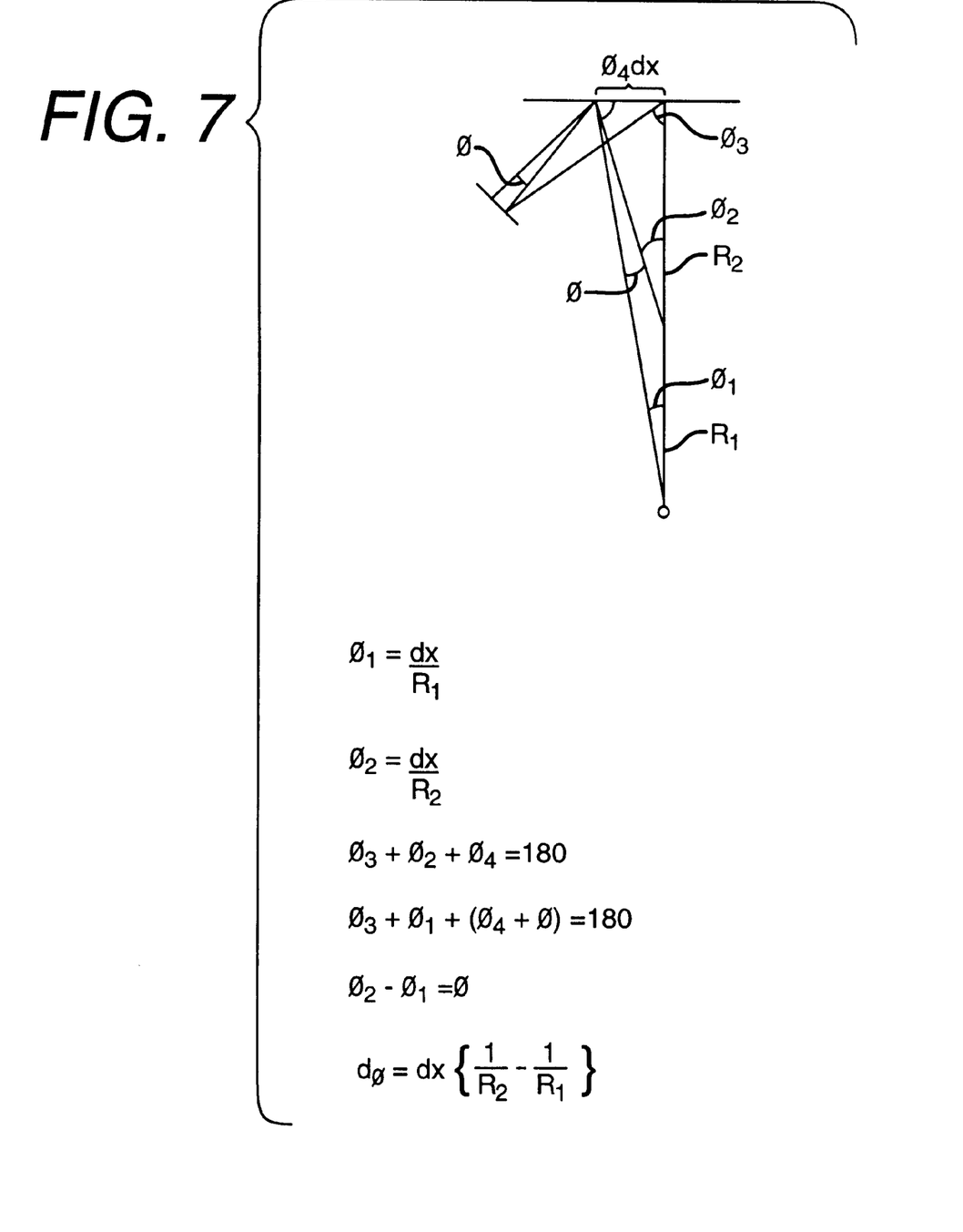
FIG. 7 is an illustration of the source of the aberration error at the focus due to the difference in direction between rays reflected from neighboring points on the logarithmic spiral and the corresponding real crystal.

$A_{LS}$, and $R_{0,LS}$ are defined by $\phi$ and $\overline{F_0 M_0}$ in equation 12. Recognizing that the aberration error at the focus is due to the difference in direction between rays reflected from neighboring points on the LS and the corresponding real crystal (see FIG. 7), one can write the integrated error for half of the monochromator $\Phi$ as:

$$\Phi = \int_0^{M_1} \left[\frac{1}{R_{cryst}} - \frac{1}{R_{LS}}\right] ds = \frac{A_{LS} \tilde{M}_1^4}{24 R_0^4} + O\left[\frac{\tilde{M}_1^5}{R_0^5}\right], \quad (16)$$

where it is understood that $M_1$ is measured along the s axis, $M_1$ is the effective endpoint closest to the focus on the surface of the monochromator crystal, $R_0$ is the monochromator crystal radius of curvature at the center of the bending axis, and the following expansions have been used:

$$\frac{1}{R_{cryst}} = \frac{1}{R_0}\left[1 - (A_{cryst} - B_{cryst})s + (A_{cryst} - B_{cryst})A_{cryst}s^2 - \right. \quad (17)$$

$$\left. \left(\frac{(B_{cryst} - A_{cryst})}{6R_0^3} + (A_{cryst} - B_{cryst})A_{cryst}^2\right)s^3\right] + O(s^4)$$

$$\frac{1}{R_{LS}} = \frac{1}{R_0}[1 - A_{LS}s + A_{LS}^2 s^2 - A_{LS}^3 s^3] + O(s^4) \quad (18)$$

Using $$M_1 = \overline{F_0 M_0} \frac{\sin\left(\frac{\omega}{2}\right)}{\sin\left(\varphi + \frac{\omega}{2}\right)}, \quad (19)$$

we arrive at the significant result that $$\Delta = 2\Phi \overline{F_0 M_0} = \frac{1}{12} A_{LS}(\overline{F_0 M_0}) \left[\frac{\sin\left(\frac{\omega}{2}\right)\sin(\varphi)}{\sin\left(\varphi + \frac{\omega}{2}\right)}\right]^4. \quad (20)$$

Using $\phi=0.238$ radians and $\overline{F_0 M_0}=165$ mm, equation 12 gives $A_{LS}=5.89E-3$. With $\omega=0.045$ radians, the best match between our mechanical approximation and the ideal logarithmic spiral curve the size of the focus is only 5E-3 microns (equation 12). Without a linear taper in the crystal monochromator width, the focal size using the same exemplary geometry would be 20 microns for a crystal of the same dimensions.

We recognize that, due to uncertainties in the shaping of the monochromator taper, this ideal condition may not be met. The uniqueness of this instrument is that the four-point bender is used to correct for these shape errors. We shall assume that the error can be corrected to first order by setting the unequal loads such that $A_{cryst}-B_{cryst}=A_{LS}$ in equation 17. For this case where the taper in the crystal deviates slightly from the ideal case, the best focus that can be achieved is given by:

$$\Phi = \frac{A_{LS}(A_{cryst} - A_{LS})}{3R_0} M_1^3. \quad (21)$$

In practice, the major factor in deforming the quality of the focus is due to the finite error associated with grinding the sides of the monochromator crystal. Recognizing that $A_{cryst}$ is the tangent of the convergence angle for the width of the monochromator, a conservative estimate for the grinding precision is on the order of 0.001 radians. Setting $A_{cryst}-A_{LS}=0.001$, $A_{LS}=5.89E-3$ radians, $M_1=15$ mm and adjusting the bending loads such that $A_{cryst}-B_{cryst}=0$, equation 20 and 21 defines the focus size of 3.1 microns.

Application to Lipid Membrane Structure. The invention can be used to determine the electron density profile in lipid bilayers with applications in the field of drug testing. Compared to the standard methods of x-ray diffraction from bilayer stacks, the use of angle dispersive x-ray diffraction as described herein is cost-effective, enables faster data collection times, permits straightforward sample preparation and may be easily adapted for batch sampling processing for screening of a large number of samples.

Two methods are currently employed in the prior art to collect the x-ray intensity generated by diffraction of the lipid bilayer as a function of the scattering angle for the lamellar systems. In the simplest case, the multilayer stacks of the lipid bilayers are centrifuged from vesicles in an aqueous medium and spun down onto a flat substrate; they are found to spontaneously align with the stacking axis normal to the substrate surface. The substrate is then mounted on a goniometer which rotates the sample to an angle $\theta$ with respect a fixed x-ray beam while the reflected intensity is collected on either a scintillation detector rotated to angle $2\theta$ with respect to the incident beam or linear position-sensitive x-ray detector. This method has the advantage that with monochromatization and collimation of the x-rays, high resolution with low background allows a high quality electron density profile to be extracted. The drawback is that the intensity must be collected at each scattering angle individually, leading to long collection times on the order of hours.

In the second prior art method, the sample is prepared in the same fashion as described above; however, the substrate is made from a bendable aluminum foil which is then mounted on a curved surface with a radius of curvature of about 20 mm. The incident beam is then focused with a curved grazing incidence mirror to illuminate the curved surface with an intense beam of low angular divergence. Different parts of the incident beam intersect the curve surface at different angles of incidence, and the scattering from the entire beam is measured on a position-sensitive x-ray detector. The advantage to this arrangement is the speed and simplicity of data collection. The entire scattering curve is collected over the desired range of angles simultaneously without the need for goniometer motion control. The disadvantage to this approach is that the beam is not truly monochromatic, but composed mainly of the $K_{\alpha 1}$ and $K_{\alpha 2}$ doublet over a background of primarily lower energy x-rays. Scattering from the low energy x-ray tail distribution as well as off-specular diffuse scattering increases the background noise and can obscure weaker diffraction lines. Furthermore, the mounting of samples is time-consuming and subject to errors associated with buckling of the substrate during mounting. While the position sensitive detection increases the speed of data collection, one must also account for x-ray intensity distributions across the beam reflected from the focusing mirror.

The present invention provides a means of measuring electron density in lipid bilayers that represents an improvement over the current prior art methods. The apparatus is shown generally in FIG. 1. The instrument may be set up to illuminate a stack of lipid bilayers centrifuged down to a flat smooth substrate (for example, a glass slide or polished Si wafer). The lipids align with their lamellar stacks oriented along the surface normal, creating a system with one-dimensional ordering along the normal to the flat substrate.

Rather than using aluminum substrates which are subsequently glued to curved cylindrical surface as described in the prior art, the lipids may be centrifuged down onto inexpensive glass substrates no more than 10 mm on a side or in diameter. The entire diffraction apparatus may then be sealed and flushed with dry helium to reduce air scattering and attenuation of the x-ray beam. The sample may be housed in a separate chamber which will be temperature controlled by water circulation and through which dry He and water-saturated He can be flowed in variable proportions to adjust the relative humidity in the lipid matrix.

X-rays from a conventional copper x-ray tube may be simultaneously monochromatized and focused onto a flat substrate onto which the lipids have been deposited. The monochromator is bent to approximate a logarithmic spiral along the bending axis according to the methodology described hereinabove. This shape ensures that the focus is of high quality and that the beam incident on the sample will be only the $K_{\alpha 1}$ component from the Cu x-ray tube source. The invention can measure the diffraction intensity over a range of angles, $\theta_{diff}$, simultaneously. From previous studies of these systems, the scans need to be extended to the range of at least 6°. In certain cases, the range must be extended by tilting the sample, while the diffraction intensities are indexed in a storage file as a function of the vector k, defined by:

$$k \equiv \frac{4\pi \sin\theta_{diff}}{\lambda}. \tag{22}$$

The data may be indexed in the storage file as a function of the scattering vector. As opposed to longer date accumulation times at two or three sample angles as is conducted in the prior art, the scanning mode ensures that each resolution element within the fan of radiation is used to accumulate the scattering intensity at a given angle. The data collection scheme precludes the need to measure the intensity profile across the radiation fan.

Once the raw diffraction data are collected, the data analysis may be fully automated. The diffraction intensities of the swollen films may be used to calculate the phase of the scattering amplitude for a given diffraction peak by least squares analysis. Once the phases are known, the relative electron densities can be calculated for the lipid bilayer by a discrete Fourier transform. The density can be normalized to the maximum density in the layer for purposes of comparison with other bilayer systems.

In one embodiment, the lipid vesicles are incubated with a candidate drug before centrifugation into the lamellar stack in order to determine the hospitality of the lipid matrix for that candidate. After centrifugation and angular dispersive x-ray diffraction analysis, the bilayer system treated with a drug candidate may be compared with the control standard; any statistical difference in the electron density profile is an indication that the drug is incorporated in the membrane. Further analysis can be used to determine the localization. The interested reader is directed to Mason and Trumbore, which is hereby incorporated by reference, for further detail on the analysis of drug localization.

Additional applications related to lipid research is the possibility of using the angular dispersive x-ray as a method for determination of drug/lipid compatibility in a combinatorial process. The small sample spot size of the beam makes the angular dispersive x-ray amenable to small area illumination, for example on a sample tray containing a large number of samples.

Application to Epitaxial Film Structure Determination and Growth. In another aspect of the invention, the angular dispersive x-ray apparatus of the invention may be adapted for use in the rapid elucidation of structure and lattice mismatch in epitaxial films. With the growing variety of epitaxial methods to prepare epitaxial and superlattice structures of metals, semiconductors and insulators comes the increasing need to find efficient and rapid in situ methods of monitoring and controlling the growth process. The deficiencies of the prior art which have been discussed in the Background of the Invention include imprecision due to wide detector slits and complicated and time-consuming data collection methods.

The apparatus and method of the present invention combine the advantages of partial reciprocal space mapping with speed of data collection. The present invention will permit data collection concerning the lattice mismatch and super-lattice period of a growing epitaxial layer in times on the order of 1 second. The invention may be configured in accordance with FIG. 1 to illuminate a substrate with an epitaxial grown film at high angles corresponding to diffraction which probes interatomic spacings. The angular interval covered by the focusing optics is sufficient to encompass diffraction from both the substrate, used for reference purposes, and the epitaxial layer. X-rays from a conventional copper x-ray tube may be simultaneously monochromatized and focused onto the growing epitaxial layer. The monochromator is bent to approximate a logarithmic spiral along the bending axis according to the methodology described hereinabove. The monochromatic beam is convergent on the sample within an envelop of $\Delta(\Omega)$ and is simultaneously diffracted within an envelop of $\Delta(2\Omega)$ onto a position sensitive detector. Typical values of the $\Delta(\Omega)$ envelop may be about 2°, and the incident angle of $\Omega$ about which the source is centered depends on the reflection of interest and the constraints imposed by the surrounding epitaxial equipment. The $\Omega$ may vary over a wide range and may typically range from about 15° to over 50°. The only moving part is a slit positioned between the x-ray source and the curved monochromator crystal. The slit may be left open for dispersive, real time mode or narrowed for reciprocal space mapping. The apparatus may optionally include in-situ reciprocal space mapping capability. The system further may be integrated into a conventional film deposition system, such a metalorganic chemical vapor deposition (MOCVD) system or physical vapor depositions systems, such as molecular beam epitaxy, laser ablation, ion beam sputtering, reactive evaporation, e-beam evaporation and the like.

This method is superior to conventional rocking curve approaches since the diffraction intensities are measured simultaneously and registered on a position-sensitive detector. Furthermore, due to the rapid data collection, the diffractometer may be used to accumulate diffraction intensities during deposition. The rapid intensity determination may then be used to control the deposition characteristics in order to control the film structure.

Surface Mapping. Because of the fine focusing characteristics of this invention, x-ray diffraction may be performed on a lateral scale on the order of microns, which is not currently feasible with current laboratory x-ray sources. For further lateral resolution perpendicular to the focusing plane, the invention may be equipped with a focusing device perpendicular to the monochromator. Because the diffraction is measured in the plane of incidence corresponding to that of the monochromator, the alternate focusing may be performed by a curved mirror, or another curved monochromator (either synthetic multilayer or single crystal type).

Film Thickness Measurement. The invention may be used to measure the thickness and density of thin films (up to about 200 nm in thickness) by using the convergent x-ray beam from the monochromator to illuminate a thin film covered substrate at grazing incident angles (0–0.3°) and measuring the x-ray reflectivity on the position sensitive detector. One observes interference maxima and minima as a function of angle and these can be related directly to the film thickness and density by the modified Bragg equation:

$$\theta^2_{max,min} = 2\delta + N^2 \left[ \frac{\lambda^2}{4d^2} \right], \quad (23)$$

where $\theta$ is the angle at which a maximum or minimum in the reflectivity occurs, $\lambda$ is the x-ray wavelength, d is the film thickness and $\delta$ is the real correction to the x-ray index of refraction; this term is on the order of $10^{-6}$ and in a direction proportional to the film density. N is used to index the maxima and minima in the reflectivity, and will have the values 1, 2, 3 . . . for $\theta_{max}$. and 0.5, 1.5, 2.5, . . . for $\theta_{min}$..

Because the x-ray reflectivity is measured simultaneously over a range of angles, the data collection is orders of magnitude faster than the conventional x-ray reflectivity scan, in which the reflection intensity is measured one angle at a time. This makes it possible to use the thickness derived from our invention to perform real-time in situ control of film thickness as a part of a larger deposition system. Film deposition systems which are known in the art may be adapted to accommodate the thickness measuring apparatus and method of the invention. The system may be integrated into a conventional film depostition system, such a metalorganic chemical vapor deposition (MOCVD) system or physical vapor depositions systems, such as molecular beam epitaxy, laser ablation, ion beam sputtering, reactive evaporation, e-beam evaporation and the like. The interested reader is referred to Luken et al for further information on the in situ growth monitoring of crystallographic layers, which is hereby incorporated by reference.

What is claimed is:

1. An x-ray spectrometer, comprising:
   an X-ray source;
   a curved crystal monochromator which focuses a monochromatic x-ray beam onto a sample surface, the curved crystal monochromator comprising a shape which is substantially identical to a logarithmic spiral and having a width that is tapered along the arclength s of the crystal; and
   a position-sensitive x-ray detector.
2. The x-ray spectrophotometer of claim 1, wherein the size of the focus of the x-ray beam onto the sample surface is less than or equal to about 3.1 microns.
3. The x-ray spectrometer of claim 1, wherein the curved crystal monochromator has a taper selected to minimize a third order difference in arclength s between an ideal logarithmic curve and the curved crystal.
4. The x-ray spectrophotometer of claim 1, wherein the size of the focus of the x-ray beam onto the sample surface is less than 20 microns.
5. The x-ray spectrometer of claim 1, monochromator crystal wherein the taper is less than about 100 milliradians.
6. The x-ray spectrometer of claim 1, wherein a linear position-sensitive proportional detector is used.
7. The x-ray spectrometer of claim 1, wherein the monochromator comprises a single crystal selected from the group consisting of germanium, silicon and lithium fluoride and multilayers thereof.
8. The x-ray spectrometer of claim 1, wherein a linear photodiode array is used.
9. The x-ray spectrometer of claim 1, wherein a linear charge coupled device is used.
10. The x-ray spectrometer of claim 1, wherein a 2-dimensional proportional x-ray detector is used.
11. The x-ray spectrometer of claim 1, wherein a 2-dimensional charge coupled device is used.
12. The x-ray spectrometer of claim 1, further comprising:
    at least one single slit positioned between the source and the monochromator.
13. The x-ray spectrometer of claim 12, wherein a plurality of slits are positioned in front of the monochromator.
14. The x-ray spectrometer of claim 1, wherein the taper is a linear taper.
15. A curved crystal monochromator which focuses a monochromatic x-ray beam onto a sample surface, wherein the width of the curved crystal monochromator is linearly tapered along an arclength s of the crystal.
16. The monochromator of claim 15, wherein the curved crystal monochromator has a taper selected to minimize a third order difference in arclength s between an ideal spiral curve and the curved crystal.
17. The monochromator of claim 15, wherein the monochromator crystal taper is less than about 20 milliradians.
18. A method for measuring electron density in a lipid layer, comprising:
    providing an x-ray source comprising an x-ray source, a curved crystal monochromator which focuses a monochromatic x-ray beam onto a sample surface, the curved monochromator comprising the shape of a logarithmic spiral and having a width that is tapered along the arclength s of the crystal, and a position-sensitive x-ray detector;
    providing a sample comprising a single of multilamellar lipid layer deposited on a flat substrate; and
    exposing the sampler to the focused x-ray beam of the x-ray spectrometer.
19. The method of claim 18, wherein the sample comprises natural or synthetic lipids.
20. The method of claim 18, wherein the sample comprises natural or synthetic lipids deposited by centrifugation from solution or suspension.
21. The method of claim 18, wherein the sample comprises a lipid deposited by Langmuir-Blodgett deposition.
22. The method of claim 18, wherein the sample comprises a lipid deposited by self-assembly from solution.
23. The x-ray spectrometer of claim 1, further comprising a sample.
24. The x-ray spectrometer of claim 1, wherein the sample comprises an epitaxially grown layer.
25. The x-ray spectrometer of claim 1, wherein the sample comprises a evaporated layer.
26. The x-ray spectrometer of claim 1, wherein the sample comprises an epitaxially grown multilayer or superlattice.
27. The x-ray spectrometer of claim 1, wherein the sample comprises a multilayer deposited by evaporation.
28. The x-ray spectrometer of claim 1, wherein the spectrometer is attached as an accessory to a larger film deposition system.
29. The x-ray spectrometer of claim 28, wherein the film parameters determined by the spectrometer may be used to control the deposition of a film.
30. The x-ray spectrometer of claim 1, wherein the spectrometer is oriented to measure x-ray reflectivity from horizontal surfaces.

31. The x-ray spectrometer of claim 1, wherein the spectrometer is adapted for scanning in the lateral direction.

32. The x-ray spectrometer of claim 1, further comprising:

a second focusing device positioned so as to focus in the plane substantially perpendicular to the curved crystal monochromator.

33. The x-ray spectrometer of claim 32, wherein the second focusing device comprises a curved mirror.

34. The x-ray spectrometer of claim 32, wherein the second focusing device comprises a curved crystal monochromator.

35. A method of measuring diffraction intensities from oriented samples in real time, comprising;

providing an x-ray spectrometer comprising an x-ray source, a curved crystal monochromator which focuses a monochromatic x-ray beam onto a sample surface, the curved monochromator comprising the shape of a logarithmic spiral and having a width that is tapered along the arclength s of the crystal, and a position-sensitive x-ray detector; and providing a crystallographically oriented sample;

exposing the sample to the focused beam of the x-ray spectrometer; and measuring the diffraction intensity at the position-sensitive detector.

36. The method of claim 18 or 35, wherein the taper is a linear taper.

* * * * *

UNITED STATES PATENT AND TRADEMARK OFFICE
CERTIFICATE OF CORRECTION

PATENT : 5,923,720
DATED : July 13, 1999
INVENTOR(S) : Scott W. Barton et al

It is certified that error appears in the above-identified patent and that said Letters Patent is hereby corrected as shown below:

On title page, under Other Publications, in reference beginning with "Tsuchiya et al.," replace "grwoth" with --growth--;

At col. 4, line 40, before "width" insert --the--;

At col. 10, line 1, replace "longarithmic" with --logarithmic--;

At col. 10, line 49, delete "(the change in bending moment of inertia along the taper)";

At col. 10, line 54, before "from" insert --(the change in bending moment of inertia along the taper)--;

At col. 10, in equation (15), delete "R" (in both instances) and insert --$R_{cryst}$--(in both instances)--;

At col. 10, in equation (15), delete "." and insert --, where $O$ stands for "terms on the order of"--;

UNITED STATES PATENT AND TRADEMARK OFFICE
CERTIFICATE OF CORRECTION

PATENT NO. : 5,923,720
DATED : July 13, 1999
INVENTOR(S) : Scott W. Barton, et al It is certified that error appears in the above-indentified patent and that said Letters Patent is hereby corrected as shown below:

At col. 11, in equation (16), delete "$\tilde{M}_1$" (in both instances) and insert --$M_1$--(in both instances)--;

At col. 13, line 35, replace "date" with --data--;

At col. 15, line 62, before "monochromator" insert --wherein the--;

At col. 15, line 63, delete "wherein the";

At col. 16, line 54, replace "a" with --an--;

At col. 17, line 13, replace ";" with --:--;

Signed and Sealed this

Third Day of April, 2001

*Attest:*

NICHOLAS P. GODICI

*Attesting Officer*  Acting Director of the United States Patent and Trademark Office